(12) United States Patent
Meyer

(10) Patent No.: US 6,389,880 B1
(45) Date of Patent: May 21, 2002

(54) ZERO SHIFT COMPENSATION OXYGEN SENSOR

(75) Inventor: Emilio Meyer, Assago (IT)

(73) Assignee: Panametrics, Inc., Waltham, MA (US)

( * ) Notice: Subject to any disclaimer, the term of this patent is extended or adjusted under 35 U.S.C. 154(b) by 0 days.

(21) Appl. No.: 09/805,302

(22) Filed: Mar. 13, 2001

(51) Int. Cl.[7] .......................... G01N 27/74; G01N 25/20
(52) U.S. Cl. ...................................... 73/25.02; 436/147
(58) Field of Search ............................ 73/25.01, 25.02; 436/147

(56) References Cited

U.S. PATENT DOCUMENTS

| | | | | |
|---|---|---|---|---|
| 3,616,679 A | * | 11/1971 | Meyer et al. | 73/25.02 |
| 4,563,894 A | * | 1/1986 | Karrer | 73/24.01 |
| 4,893,495 A | * | 1/1990 | Meyer | 73/25.02 |
| 5,012,669 A | * | 5/1991 | Meyer | 73/25.02 |
| 5,269,170 A | * | 12/1993 | Meyer | 73/25.02 |
| 5,356,819 A | * | 10/1994 | Ritschel | 436/147 |
| 6,112,576 A | * | 9/2000 | Tsopelas et al. | 73/25.02 |

* cited by examiner

Primary Examiner—Hezron Williams
Assistant Examiner—Jay L. Politzer
(74) Attorney, Agent, or Firm—Iandiorio & Teska

(57) ABSTRACT

A magnetic wind oxygen sensing device provides a local magnetic field defined by magnetic pole pieces, and employs a plurality of thermal elements in a bridge in the local magnetic field to measure oxygen concentration in a surrounding gas mixture, creating a magnetic wind and determining the thermal effects induced in sensing elements as a result of the wind. A pair of sensing elements are positioned such that one lies upstream and one downstream of each wind generator, and both are substantially in thermal equilibrium with adjacent gas so they are unaffected by changes in thermal capacity of background gas components. When oxygen is present, the two sensing elements are passively cooled below, and heated above the temperature set by a local heater, respectively. In the absence of oxygen, the sensors reside at the same temperature, so they are self zero-ing, and this zero point does not shift when background gases with differing thermal characteristics are present. The arrangement is also immune to thermal creep and changes in physical position of the sensing elements that would otherwise introduce bridge asymmetries, offsets and drift artifacts.

12 Claims, 4 Drawing Sheets

ZERO SHIFT COMPENSATION OXYGEN SENSOR

BACKGROUND OF THE INVENTION

This invention relates to sensors and systems for measuring the concentration of oxygen present in a mixture of gases, wherein the sensor relies upon detection of thermal effects due to a wind formed in a magnetic field within the measuring device as a result of the paramagnetism of oxygen present in the mixture. A variety of such devices have been described for measuring oxygen concentration, and these magnetic wind oxygen sensing systems rely on the fact that when placed in a magnetic field, the paramagnetic oxygen will exert a pressure in a certain direction, while the remaining components of the mixture, which is substantially formed of diamagnetic gases, are unaffected by the local field. A mixture of oxygen with diamagnetic gases behaves, from the magnetic point of view, as a single component with a magnetic property (magnetic susceptibility) equal to the weighted average of the susceptibilities of each of the components.

One type of apparatus of this sort measures the concentration of oxygen by relying upon the inverse relationship between temperature and the magnetic susceptibility of oxygen, and provides a heater to raise the temperature of a portion of an oxygen-containing mixture in a local region of a magnetic field, producing a pressure differential that gives rise to a directional wind. The wind has a magnitude that depends on the local field, the local temperature differential or thermal gradient, and the level of oxygen. By arranging heating and heat sensing elements in close proximity so that movement of the wind carries heat or selectively cools one or another of the components, the magnitude of this wind, or its functional relationship to the oxygen concentration, may be calibrated.

A number of prior publications and patents describing instruments which exploit one or more of these effects are referenced in applicant's earlier U.S. Pat. No. 5,269,170 issued Dec. 14, 1993; U.S. Pat. No. 5,012,669 issued May 7, 1991; and U.S. Pat. No. 4,893,495 issued Jan. 16, 1990. These patents are hereby incorporated herein by reference in their entirety, and attention is particularly directed to their circuit diagrams illustrating sensing bridge and temperature or current control arrangements for balancing the bridge. Among the complicating factors which must be corrected are the problem of defining a layout or geometry such that the so-called chimney effect, the natural directional flow induced by the lesser density of heated gas, does not confound the response of the thermal elements, and the problem of compensating for the rate of cooling or heating due to specific heat or heat capacity of the background gases present in addition to the measurand. In the foregoing patents a number of constructions are proposed for addressing these factors. On a circuit level these may include the use of multiple heating or sensing elements arranged in bridges to balance or counterbalance certain effects that enjoy symmetry as a result of their spatial layout. Another useful technique involves electrically heating a portion of the assembly to a constant temperature and monitoring the current required to maintain that temperature. This current may then be used to develop a normalizing measurement to which other parameters are referenced.

However, one basic limitation of this technology resides in the fact that small heated sensing elements are employed to detect the wind. The temperature of these elements is affected not only by the magnitude of the magnetic wind induced by the heating and magnetic field structures, but also by the heat transfer characteristics of the background gases that are present. A change in background gases thus induces a shift in zero point (i.e., the output when oxygen concentration is zero) of the sensing circuitry.

Furthermore, while constructions as illustrated in the aforesaid patents have enhanced the accuracy of paramagnetic oxygen sensing systems, they rely on the use of multiple elements in bridge configurations. This typically requires that the response and characterizing parameters of the elements be quite similar, i.e., that the components be matched. Some matching of the circuit characteristics of components is generally feasible, and may initially be performed quite accurately, especially for certain thin film devices wherein hundreds or thousands of virtually identical units are fabricated in a single process on a single wafer. However, initial matching of the basic response characteristics may be insufficient to assure continued accuracy. As a practical matter, when discrete sensors such as thermistors or resistive heating elements are used, the very process of mounting and arranging their geometry within the sensing device may introduce asymmetries of response, or instabilities of location that result in asymmetries of response over time. For example, when a thermistor is mounted close to the wall of a massive magnet structure, the rate of cooling due to gas conduction between the thermistor and the wall will vary with the composition of the background gas and its thermal capacity. Further, for a given background gas, such conductive dissipation is markedly affected by even small changes in proximity to the wall, which may introduce disproportionately large conductive or radiative heat loss, or with an opposite effect, may give rise to boundary layer flow stagnation.

Various approaches have been presented in the prior art to address the dependence on background gas thermal characteristics. For example, the above-cited patents teach a method and circuitry for maintaining the bridge at a constant temperature, and carrying out adjustments to compensate for background gas effects. However, such bridge circuitry may augment the variations induced by background gas changes, and the correction circuitry may not fully correct for these background-induced variations. Moreover, facially identical components in a bridge may respond differently to the same drive current when placed in series, because their thermal dissipation characteristics are not well matched. Mismatch may occur either intrinsically in the response of the circuit elements, or because one unit of a pair is positioned fifty or a hundred micrometers differently with respect to nearby structures. The small heated elements are also inherently subject to thermal stresses and temperature cycling, causing wires to shift and local geometry to change over time, introducing asymmetric effects, such as those just described, even in sets of initially well-positioned and well-matched components.

These effects can imbalance or impair the practical effectiveness of a bridge circuit, and may result in loss of calibration.

The problem is compounded because, since extremely minute levels of force are engendered by the action of a paramagnetic gas within the magnetic field, it is necessary that the heat sensing and generating elements be sufficiently small to make the effect of the induced wind detectable. It is further desirable that the sensors be mounted in sufficiently small passages that high flux may be achieved and also that wind is effectively channeled to develop higher velocity. However, because the small thermal elements necessarily are mounted on small conductors, normal flexing, structural bending, vibration and thermal expansion effects result in migration or shifting of the actual position of the heating and sensing element. Thus their response to wind-induced thermal transfer, or the rate at which each dissipates heat, or the power required to maintain a constant temperature, resistance or signal in the element, will vary over time as well as changing with properties of the background gases. This is particularly true of constructions in which the elements are both heated to generate a wind, and also employed as sensing elements to respond to heat transferred to or from the heated element.

One approach to this problem might be to provide a strictly planar device incorporating otherwise conventional sensing bridge circuitry, i.e., to provide a small chip having resistive heating and temperature sensing elements fabricated in a very precise array on the surface of the chip. However, such a construction may introduce problems of its own. Not only may the required metallizations for an intended sensing environment be incompatible with the metallochemistry of an otherwise desirable chip technology, but the use of strictly planar devices may be ill suited to a measurement apparatus that relies on small wind effects. This is because boundary layer effects, which greatly influence the gas flow being measured near to the surface of a planar device, may be difficult to model, or have asymptotic pole or null behavior, rendering the usual physical models inapplicable or subject to variations that would prevent calibration of the response with oxygen level.

Accordingly it would be desirable to provide a paramagnetic oxygen sensing apparatus having improved stability and predictability.

It would farther be desirable to provide a magnetic wind oxygen sensing apparatus that is less prone to variation and disturbance with changing composition of background gas in which the oxygen component appears.

SUMMARY OF THE INVENTION

One or more of the above desirable ends are achieved in accordance with the present invention by a magnetic wind oxygen sensing device that provides a local magnetic field is defined, for example, by magnetic pole pieces, and has a plurality of thermal elements arranged in a bridge at the local magnetic field to measure oxygen concentration present in a surrounding gas mixture. The device creates a magnetic wind and detects thermal effects induced in the elements as a result of the wind. The wind is generated by heating elements positioned at a region of high field intensity. The heat locally reduces paramagnetism of oxygen present in the gas, causing a pressure drop compared to unheated gas of identical composition, so that cooler gas in the magnetic field displaces the warmed gas and flows over the heater elements. Each wind generator is located between two sensing elements, and these are positioned so that, while both receive heat from the wind generator, one sensor is somewhat cooled (by flowing gas from the lower temperature region of the measuring cell as a whole, sometimes simply referred to as "ambient" herein) and the other is somewhat heated, respectively, by the wind thereby generated. Significantly, in the absence of oxygen, there is no airflow, and the two sensing elements are at the same temperature (which is also the temperature of the gas immediately surrounding them), due to the heat received from the wind generator located centrally between them. As a result, the zero point remains fixed, even when conductive properties of the surrounding (but stationary) gas change. When oxygen is present, a wind arises, and the wind reduces the heat received by the upstream sensor and increases, by practically the same amount, the heat received by the downstream sensor. However, the total resistance of the two sensors remains substantially unchanged; this quantity can therefore be used to accurately control the level of the central, wind generating heater element.

Preferably the sensing elements are arranged in a bridge, and sensing is performed by detecting the resistance of the sensing elements with the elements attached to a very low current circuit, so that power dissipation in the element is negligible. The wind generator or heater elements may be powered at a variable level, responding to a feedback signal to maintain the temperature of sensing elements, or an output of a bridge circuit composed of sensing elements, at a constant level. The sensing portion may further employ a power supply that is completely independent from that of the wind generating heater elements, so that readings are unaffected by the changing level of heater power being delivered to the wind generator(s). A preferred sensor bridge is thus self zeroing, to provide a zero reading when the oxygen level is zero independently of background gas composition, and is immune to the thermal stresses that would otherwise introduce positional changes and resulting artifacts in sensor of bridge response.

BRIEF DESCRIPTION OF THE DRAWINGS

For a more complete understanding of the nature and objects of the invention, reference is made to the following detailed description and the accompanying drawings in which.

DETAILED DESCRIPTION

Figure 1:
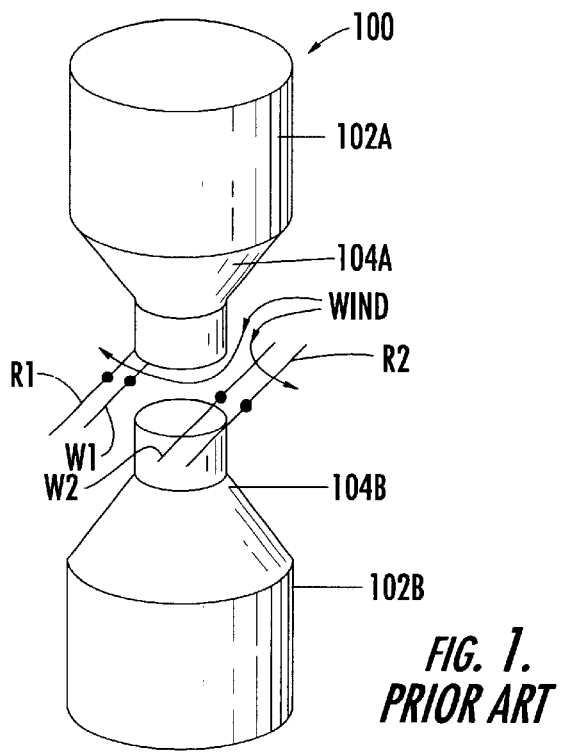
FIG. 1 is a schematic diagram depicting a bridge-type oxygen sensing cell of the prior art.

In accordance with a principal aspect of the present invention, an improved thermal magnetic wind sensor is achieved by a sensor arrangement configured to be substantially immune to variability resulting from mismatch or changing of the dissipation constant of the sensing assembly. As noted above, thermal dissipation is subject to variation when changes occur in the thermal properties of background gases, and also when extremely small displacements of circuit elements arise. In one aspect of the invention, immunity to one or more of these effects is achieved in part by providing a device of controlled geometry having surface heat or sensing elements at precise positions thereon. In another aspect, the invention separates the heating, or wind generating, and the sensing functions, so that sensing elements are not subject to evolving thermal shifting, asymmetries and stresses. In a preferred aspect, pairs sensing elements are arranged to be passively heated or cooled, while always residing near the surrounding temperature of a local measurement region, which may, for example, be maintained at a temperature only slightly above ambient. In still a fourth aspect, the invention positions sensing elements upstream and downstream, respectively, of each of a pair of heater elements in a magnetic wind, and forms a sensing bridge of the sensing elements.

The sensing elements may be symmetrically positioned surrounding the heating elements to compensate for directional effects, and may be placed in a measuring bridge circuit having a constant or a controlled temperature, and are preferably operated at a controlled current level compatible with output signal requirements, yet low enough that self-heating is below a negligible threshold. The resistance of the measuring bridge may be controlled to a constant level by changing a drive current provided to the heated wind generation elements. That is, the heat generated by the centrally positioned and separately-powered wind generating heating elements is controlled using feedback from the measuring bridge.

With this construction, when there is no oxygen present, the measuring sensors both reside at substantially the same temperature as the gas in a local region immediately surrounding the heating element (which may be set, for example to about 120° C.), so that variations in composition of background gas do not change the heat dissipation of the different sensors or shift their zero point. The measuring cell as a whole may be maintained at a temperature slightly above the gas environment, e.g., at about 100° C. When oxygen is present in the gas, the two sensors of a pair reside at slightly different temperatures, but their average temperature remains the same. Thus, even in the presence of a magnetic wind, there are only small temperature differentials, and the levels of thermal cycling are negligible.

As a result, in this configuration, the sensors do not suffer zero-offsets when the composition of non-paramagnetic gas components changes, and sensor wires are not subject to the thermal cycling and creep of the prior art construction, providing both immunity to a major environmental source of short-term change and a major physical source of long term drift.

The invention will be best understood in the context of specific illustrative embodiments, following discussion of a prior art oxygen sensor device 100, shown in FIG. 1. As shown, two pairs of electrically heated thermistors R1, W1 and R2, W2 are located at the edge of a high intensity magnetic field. The second thermistor of each pair of electrically heated thermistors, e.g., thermistors R1 or R2, is located adjacent to a corresponding wind generating heated thermistor W1 or W2, respectively, but is selectively offset outside the region of highest magnetic field intensity, illustratively adjacent to a gap defined between the pole pieces 104a, 104b of two opposed magnet portions 102a, 102b. In this arrangement, when oxygen is present in the surrounding gas, and the thermistors W1 and W2 are electrically heated, the drop in paramagnetism around the heater results in a net pressure from the magnetic region outwardly past the heater, introducing an airflow which, as indicated by arrows in the Figure, moves in the direction of the adjacent thermistor of each pair. Thus, the wind generating thermistors W1 and W2 lose heat to the adjacent thermistors R1 and R2, thus reducing the temperature of the wind generating thermistors W and increasing the temperature of the sensing thermistors R in proportion to the oxygen concentration. The above-referenced patents illustrate various sensing and drive circuits wherein the elements R1, W1, R2, W2 are connected in series in a bridge, with certain adjustable elements allowing one to compensate for different types of drift or instability.

Figure 2:
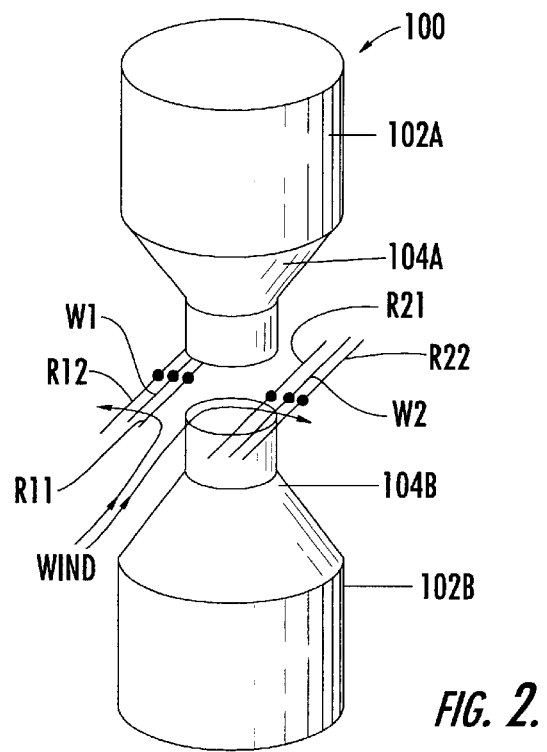
FIG. 2 is a corresponding schematic diagram depicting the oxygen sensing cell in accordance with the present invention.

In accordance with one aspect of the present invention, the structural instabilities and background gas dependencies of this arrangement are addressed by providing a wind generating and sensing arrangement as shown in FIG. 2. In accordance with this aspect of the invention, each wind generator W1 or W2 is surrounded by two sensors R11 and R12, or R21 and R22, respectively. As shown, the geometry of the sensing cell is similar to the prior art cell of FIG. 1, except that two thermistors or other sensing elements are placed on opposite sides of each wind generating element, i.e., upstream and downstream with respect to the direction of induced flow. The sensing elements are sufficiently closely-positioned to their corresponding wind generators that each pair lies at approximately the temperature set by the wind generator, i.e. they are passively heated by the wind generator and its adjacent environment.

In an illustrative embodiment, the measurement cell as a whole (i.e., the gas sample cell and magnet gap region) is set to one temperature (This may be, for example, about 100° C., somewhat above the environment generally), while the wind generating heater elements are powered to establish a higher temperature (for example, about 120° C.) in a small region immediately near the generator elements. This temperature is preferably set close to the cell temperature, but sufficiently higher that it reduces the level of paramagnetism in any oxygen that is present, and thus establishes a wind. In FIG. 2, arrows indicate generally the direction of gas flow from the central region of the cell outwardly over the sensors and wind generators. With this configuration, when oxygen is present, the upstream sensors—R11 and R21 lying in the high field gap, are at one temperature (e.g., slightly below the nominal 120° C. temperature set by the heater W1 or W2), while the downstream (outside) sensors R12 and R22 are heated slightly above that level by the wind passing from the higher pressure region in the magnetic gap outwardly over the heaters W1, W2. In essence, the local heating produced by the generator W1 or W2 is shifted outwardly, to affect the outer sensors R12 and R22 more than the inner ones.

Figure 3A:
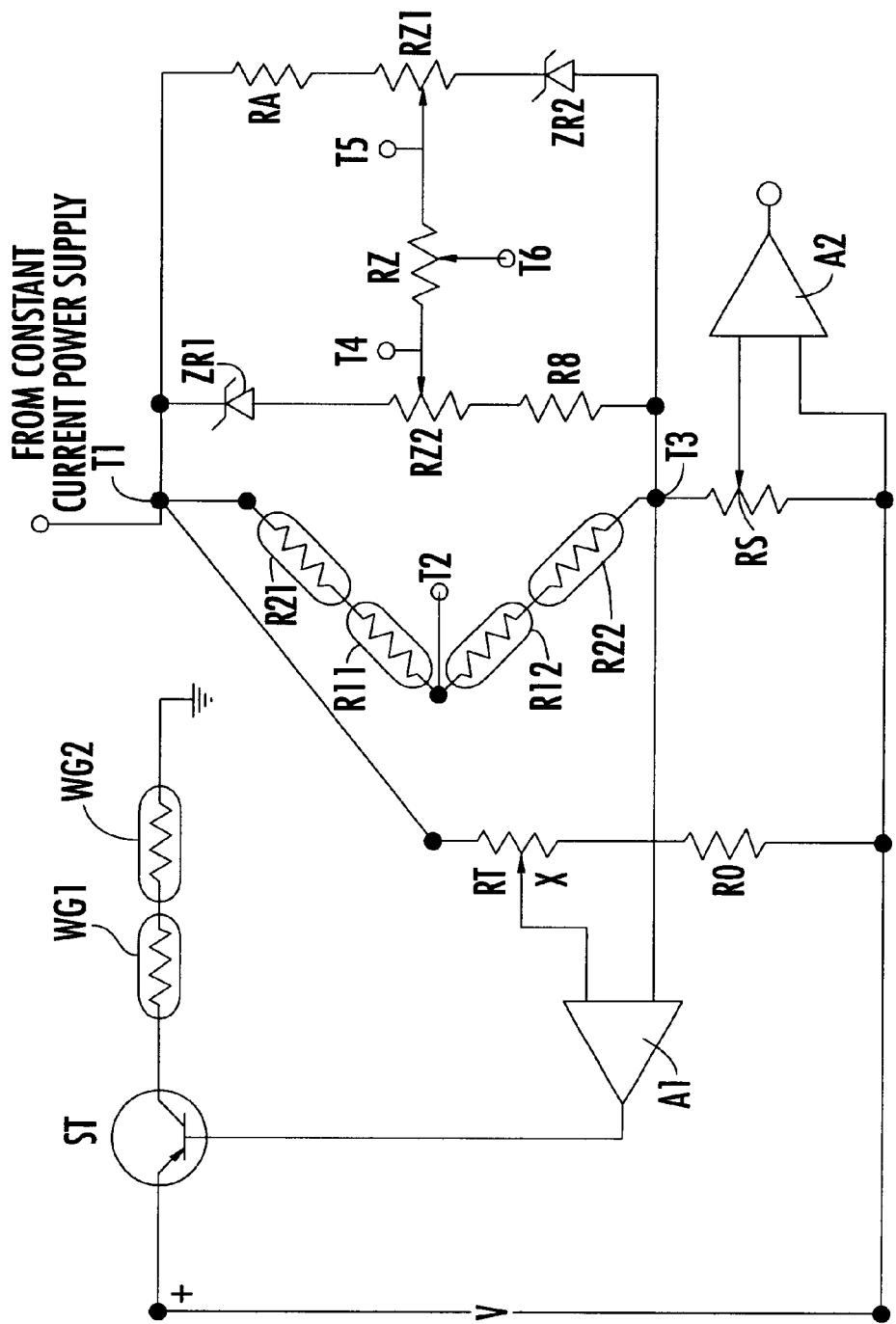
FIG. 3A illustrates one suitable sensing circuit for the practice of the invention.

Further, as described below with respect to FIG. 3A the sensing thermistors may be operated with a current circuit that is at least relatively independent of the heater draw. Preferably, the sensor current is entirely independent of the heater current, and most preferably, as indicated in FIG. 3A, the circuit may be implemented with resistive-sensing elements, such as thermistors, driven by a constant current supply, and this current is set sufficiently low that it induces negligible heating of the sensing elements. The sensing elements then passively reside at or near the temperature of the gas immediately surrounding them, so that their heat exchange with the environment is negligible and thus does not vary with changing heat capacity of the different background gas components present in the sample gas. As a result, the sensors' zero point does not shift when the background gas composition changes. Furthermore, since the total temperature difference is also both small and substantially constant, the sensor position is substantially unaffected by the type of changing heating cycles or resistively heated offsets that occur in the device of FIG. 1; and differences in alignment or position that do occur among the various sensors have relatively little influence on their relevant matching characteristics. Further, by making the resistance sensing circuit independent of the driving circuit for the heaters W1, W2, the sensor readings do not suffer secondary changes influenced by variations in the current drawn by the wind generating elements W1, W2.

Figure 3B:
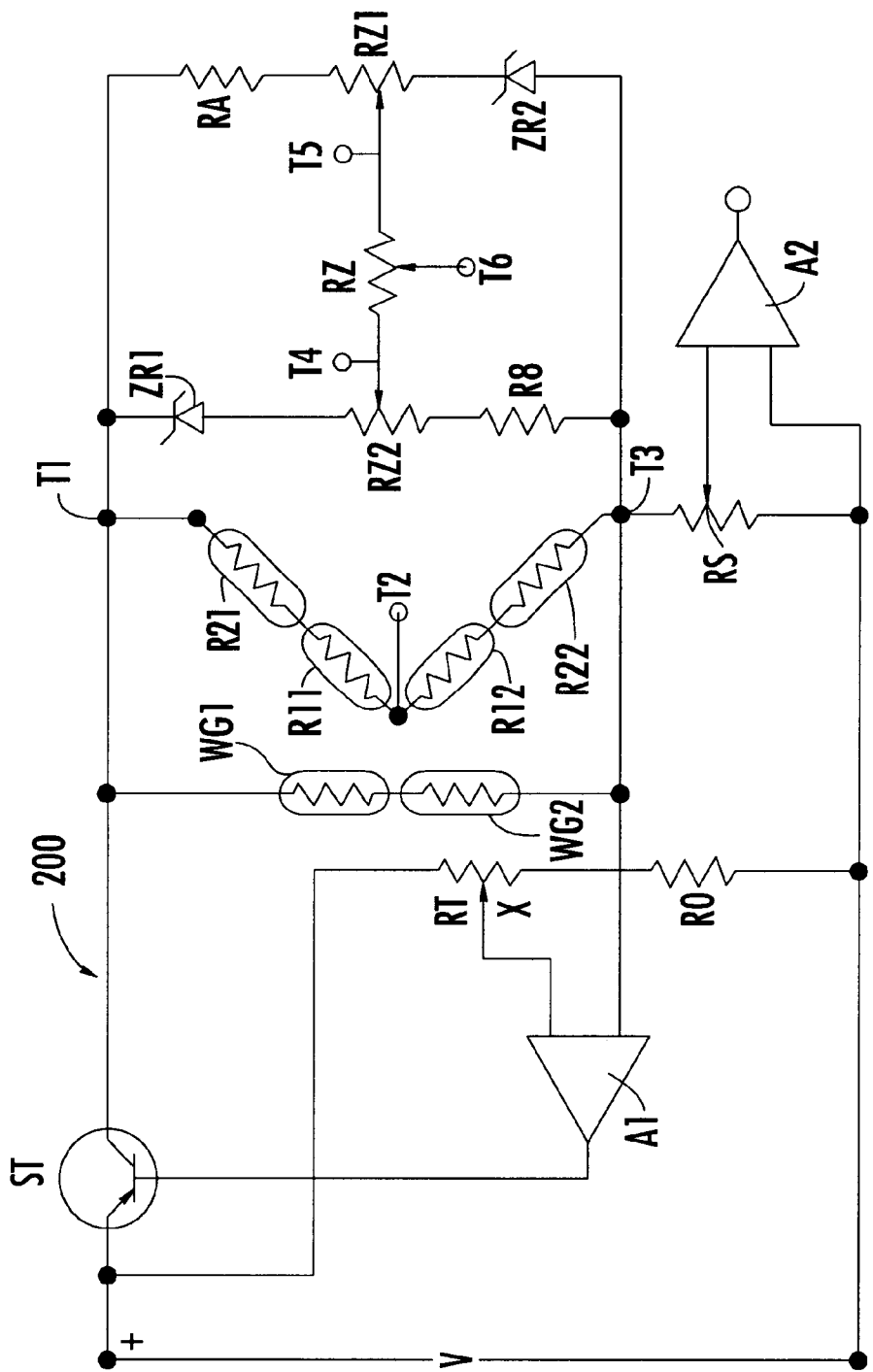
FIG. 3B illustrates another suitable sensing circuit for the practice of the invention.

FIGS. 3A and 3B show suitable circuit arrangements for achieving this operation.

As shown in FIG. 3B, a measurement circuit 200 of the invention for the measurement cell illustrated in FIG. 2 has the sensing elements R11, R12, R21, R22 serially connected. The inside sensors R11, R21 form one leg of a bridge, between power terminal T1 and terminal T2, and the outside sensors R12, R22 form another leg between T2 and terminal T3. The wind generating elements WG1, WG2, corresponding to W1, W2 of FIG. 2, are connected across T1, T3, but are independent of the sensing elements; they are in a separate current path and constitute a preponderance of the load on the circuit. As further seen in FIG. 3B, the two legs formed by the sensing elements constitute a measuring bridge circuit, which is imbalanced due to the resistance change brought about by the temperature difference between the inside (upstream) and the outside (downstream) sensors when oxygen is present in the sample gas. This imbalance, in turn, is proportional to the oxygen concentration.

Various features of this circuit may be similar to those of the circuits shown in the above-referenced U.S. patents, and reference is made thereto for a general discussion of these aspects of the circuitry. Amplifier A1 has an input referenced to potentiometer RT connected to a constant voltage source, and its output drives a transistor ST to provide an adjustable drive signal for the heating elements WG1, WG2, setting the temperature or current of these elements. The amplifier A2 senses, through resistor RS, the current change necessary to restore bridge balance, and the amplifier output may be used as a multiplier for correcting the oxygen reading obtained from the bridge.

However, advantageously, the heating or wind-generating elements in measurement cells of the present invention do not form a portion of the measuring bridge. The sensing elements may have a very high resistance so that the current through these elements is small and does not result in any noticeable intrinsic heating. They reside in substantial thermal equilibrium with the surrounding gas. As a result, there is negligible heat loss to the surrounding gas, and changes in heat capacity of the background gas have no effect on operating temperatures of the bridge elements.

FIG. 3A shows another circuit for operation of the oxygen sensing system of the present invention. In the embodiment, the wind generating heating elements WG1, WG2 are separately powered by the transistor ST based on bridge output, while a separate or independent, constant current power supply is connected across the sensing bridge circuitry. This permits extremely accurate bridge measurements, without variations due to unmatched or ill-controlled heat dissipation.

Figure 4:
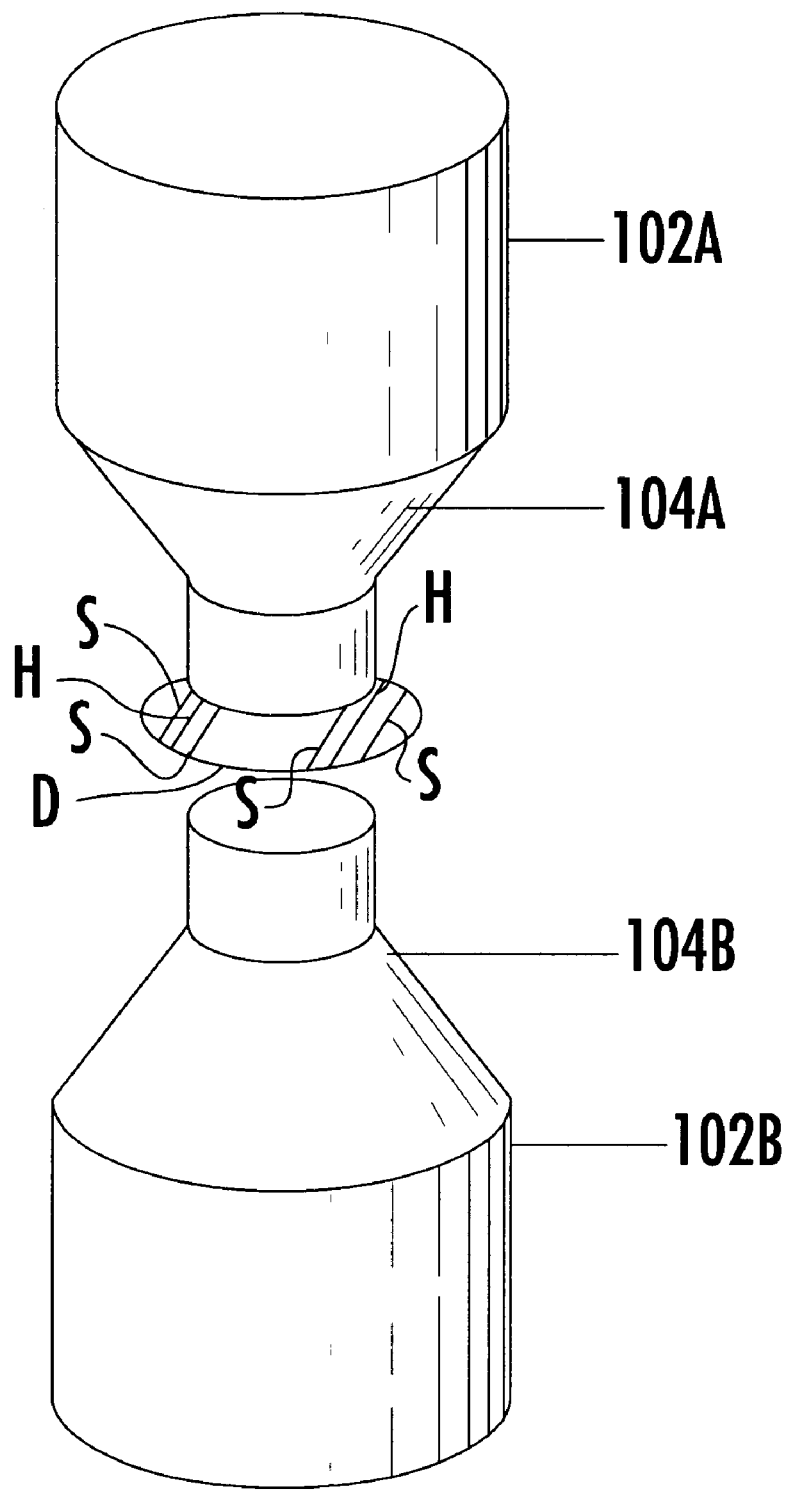
FIG. 4 illustrates a embodiment on an integrated substrate.

In accordance with another aspect of the invention, the sensing systems may be implemented with an integrated sensor assembly, such as a thin film or disk substrate sensor configuration, that defines uniform and precise sensor bridge and gap placement geometries. FIG. 4 illustrates one embodiment of this aspect of the invention. As shown, according to this aspect of the invention, a substrate, such as a thin ceramic disk D has a precisely located pattern of sensing element leads (such as platinum leads) or actual sensing elements formed thereon (e.g., by sputtering through a lithography mask), denoted generally by "S" in the Figure. Heater elements may also be formed on the substrate, but are preferably separately attached, e.g., as illustrate at positions defined by heater lead pads "H". The Figure is intended only to be schematic, and other implementations may employ posts or stand-offs for various ones of the described structures or elements to meet fabrication requirements, to better position a heater or sensor in a wind path, or to otherwise optimize the physical operation of the paramagnetic wind sensor.

In this embodiment, the provision of a chip, or disk having a fixed and highly symmetrical construction, and bearing precisely matched or identically fabricated elements, provides a precise and non-changing geometry of the various elements to prevent mismatch, thermal creep and drift in the basic operating parameters and zero points.

The invention being thus described, further variations and modifications will occur to those skilled in the art, and all such variations and modifications are considered to be within the scope of the invention, as defined herein and by the claims appended hereto, and equivalents thereof.

What is claimed is:

1. A magnetic wind oxygen sensing device operable in a local magnetic field wherein a plurality of thermal elements are arranged in a bridge in the local magnetic field to measure oxygen concentration in a surrounding gas mixture by creating a magnetic wind and determining the thermal effects induced in the elements as a result of the wind, the wind being generated by a pair of thermal heating elements which locally reduce paramagnetism of oxygen present in the gas, said device being characterized in that each said thermal heating element is surrounded by two thermal sensing elements that are arranged in a bridge and operated such that the sensing elements reside substantial in thermal equilibrium with surrounding gas so zero point does not vary with changes in composition of background gas.

2. The magnetic wind sensor of claim 1, wherein the sensing elements employ a power supply independent from that of the heating elements.

3. The magnetic wind sensor of claim 1, wherein the heating elements are variably powered so as to maintain an output of the sensing elements constant.

4. The magnetic wind sensor of claim 1, wherein the sensing elements are arranged in a self zeroing bridge configured to provide a zero reading when the oxygen level is zero.

5. The magnetic wind sensor of claim 1, wherein the sensing elements passively reside substantially at a local ambient temperature of immediately surrounding gas so that position of the elements remains immune to thermal creep and displacement, thereby enhancing long term stability of the bridge.

6. A magnetic wind oxygen sensing device operable in a local magnetic field wherein a plurality of thermal elements are arranged in a bridge in the local magnetic field to measure oxygen concentration in a surrounding gas mixture by creating a magnetic wind and determining the thermal effects induced in the elements as a result of the wind, the wind being generated by a pair of thermal heating elements which locally reduce paramagnetism of oxygen present in the gas, said device being characterized in that each of the thermal heating elements is associated with thermal sensing elements, and all thermal sensing elements operate in a bridge with sensing circuit having negligible power dissipation such that the sensing elements passively reside substantially at the temperature of adjacent gas and position of the elements remains immune to thermal creep and displacement, thereby enhancing long term stability of the bridge.

7. A magnetic wind oxygen sensing method of the type that provides a local magnetic field and a plurality of thermal elements arranged in a bridge in the local magnetic field, and measures oxygen concentration in a surrounding gas mixture by creating a magnetic wind and determining the thermal effect induced in the elements as a result of the wind, wherein the wind is generated by providing one or more thermal heating elements to locally reduce paramagnetism of oxygen present in the gas, wherein the method is characterized by providing a pair of thermal heating elements each surrounded by two thermal sensing elements arranging the sensing elements in bridge and operated with a sensing circuit having negligible power dissipation such that the sensing elements reside substantially at tie temperature of adjacent gas such that zero point does not vary with changes in composition of background gas.

8. The magnetic wind sensing method of claim 7, further comprising the step of driving the thermal heating elements with a power supply independent of the sensing circuit.

9. The magnetic wind sensing method of claim 7, further comprising the step of driving the heating elements in a feedback loop so as to maintain output of the sensing bridge constant.

10. The magnetic wind sensing method of claim 7, further comprising the step of arranging the sensing elements in a self zeroing bridge configured to provide a zero reading when the oxygen level is zero.

11. The magnetic wind sensing method of claim 7, further comprising the step of arranging the sensing elements to passively reside substantially at a constant surrounding temperature such that position of the elements remains immune to thermal creep and displacement, thereby enhancing long term stability of the bridge.

12. A magnetic wind oxygen sensing method, such method comprising the steps of arranging and operating a plurality of thermal elements in a bridge positioned in relation to a local magnetic field so as to measure oxygen concentration in a surrounding gas mixture by creating a magnetic wind and determining the thermal effects induced in the elements as a result of the wind, the wind being generated by driving a pair of thermal heating elements to locally reduce paramagnetism of oxygen present in the gas, said device being characterized by the step of providing a set of thermal sensing elements including respective pairs of sensing elements configured in a bridge and operated with a sensing circuit, wherein the sensing elements reside substantially in thermal equilibrium with a substantially constant local temperature, so that position of the elements remains immune to thermal creep and displacement, thereby enhancing long term stability of the bridge.

* * * * *